(12) United States Patent
Kessler et al.

(10) Patent No.: US 10,361,376 B2
(45) Date of Patent: Jul. 23, 2019

(54) PROAZAPHOSPHATRANES AS N-DOPANTS IN ORGANIC ELECTRONICS

(71) Applicant: Siemens Aktiengesellschaft, Munich (DE)

(72) Inventors: Florian Kessler, Hoechstadt an der Aisch (DE); Sébastien Pecqueur, La Couture (FR); Guenter Schmid, Hemhofen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 15/544,244

(22) PCT Filed: Dec. 8, 2015

(86) PCT No.: PCT/EP2015/078921
§ 371 (c)(1),
(2) Date: Jul. 17, 2017

(87) PCT Pub. No.: WO2016/116205
PCT Pub. Date: Jul. 28, 2016

(65) Prior Publication Data
US 2018/0006240 A1 Jan. 4, 2018

(30) Foreign Application Priority Data
Jan. 19, 2015 (DE) ........................ 10 2015 200 690

(51) Int. Cl.
*H01L 51/00* (2006.01)
*C07F 9/6584* (2006.01)
(Continued)

(52) U.S. Cl.
CPC ........ *H01L 51/0069* (2013.01); *C07F 9/6584* (2013.01); *C07F 9/65848* (2013.01);
(Continued)

(58) Field of Classification Search
None
See application file for complete search history.

(56) References Cited

U.S. PATENT DOCUMENTS

| 8,859,110 B2 | 10/2014 | Fuchs et al. | 428/690 |
| 2015/0060804 A1 | 3/2015 | Kanitz et al. | 257/40 |

(Continued)

FOREIGN PATENT DOCUMENTS

| DE | 102012217587 A1 | 3/2014 | ............. C07C 13/15 |
| JP | 2006023562 A | * 1/2006 | |

(Continued)

OTHER PUBLICATIONS

English text machine translation for Ogaki et al. (JP 2006-023562 A), accessed from the JPO AIPN website, copy attached to the case file as a PDF, pp. 1-35. (Year: 2006).*

(Continued)

*Primary Examiner* — Katie L. Hammer
(74) *Attorney, Agent, or Firm* — Slayden Grubert Beard PLLC

(57) ABSTRACT

An organic n-dopant for doping organic electron transport materials. The n-dopant comprising at least one proazaphosphatrane compound having a triple N-substituted phosphorus atom of the formula

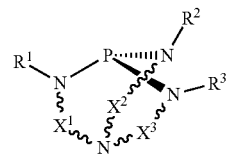

6 Claims, 1 Drawing Sheet

(51) Int. Cl.
    *H01L 51/05*       (2006.01)
    *H01L 51/42*       (2006.01)
    *H01L 51/50*       (2006.01)

(52) U.S. Cl.
    CPC ...... *H01L 51/0545* (2013.01); *H01L 51/4293* (2013.01); *H01L 51/5076* (2013.01)

(56) References Cited

U.S. PATENT DOCUMENTS

| | | | |
|---|---|---|---|
| 2015/0243889 A1 | 8/2015 | Schmid et al. | 438/99 |
| 2017/0098787 A1 | 4/2017 | Maltenberger et al. | 556/64 |

FOREIGN PATENT DOCUMENTS

| | | | |
|---|---|---|---|
| JP | 2006023562 A | 1/2006 | G03G 5/05 |
| JP | 2013181072 A | 9/2013 | C08G 73/02 |
| KR | 20150001747 A | 1/2015 | C09K 11/06 |
| WO | 2016/116205 A1 | 7/1916 | C07F 9/6584 |
| WO | 2009/153276 A1 | 12/2009 | C07F 9/6581 |
| WO | 2012/175219 A1 | 12/2012 | C07F 9/06 |
| WO | 2013/182389 A2 | 12/2013 | H01L 51/00 |

OTHER PUBLICATIONS

Núñez, Andrés et al., "Bell-Shaped pH-Rate Profile in a Reaction Involving a Pentacoordinated Phosphorus Intermediate," Journal of Organic Chemistry, vol. 61, pp. 8386-8390, Apr. 18, 1996.

Ishikawa, Tsutomu, "Superbases for Organic Synthesis—Guanidines, Amidines, Phosphazenes and Related Organocatalysts," Wiley, ISBN: 978-0-470-51800-7, 340 Pages, 2009.

Chatelet, Bastien et al., "Superbases in Confined Space: Control of the Basicity and Reactivity of the Proton Transfer," Journal of the American Chemical Society, vol. 135, No. 49, pp. 18659-18664, 2013.

German Office Action, Application No. 102015200690.5, 9 pages, dated Aug. 11, 2015.

International Search Report and Written Opinion, Application No. PCT/EP2015/078921, 16 pages, dated Mar. 17, 2016.

Chinese Office Action, Application No. 201580073923.2, 12 pages, dated Jul. 20, 2018.

Korean Office Action, Application No. 2019026056847, 6 pages, dated Apr. 10, 2019.

\* cited by examiner

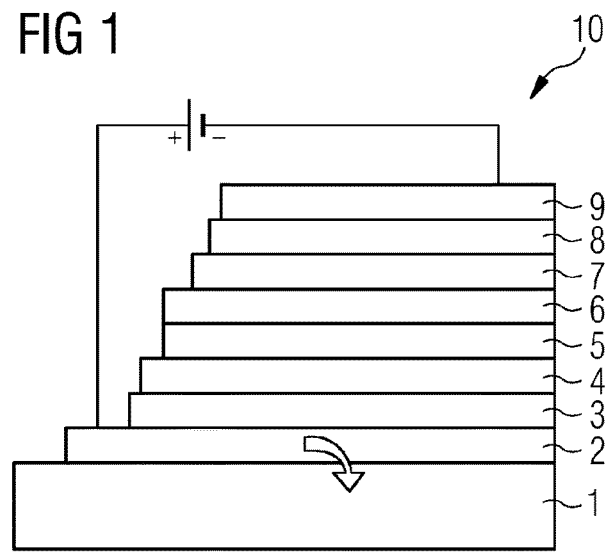
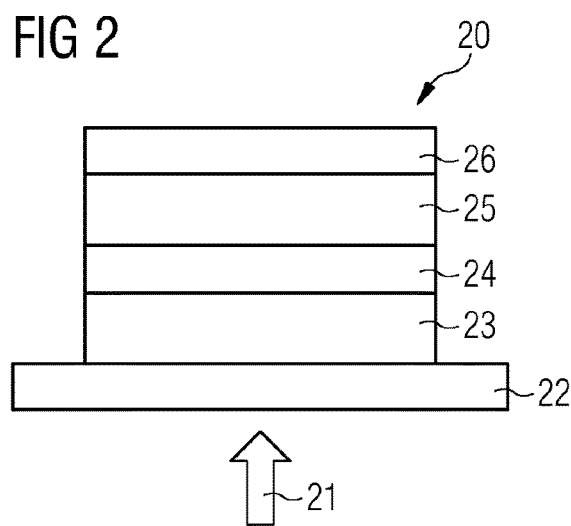
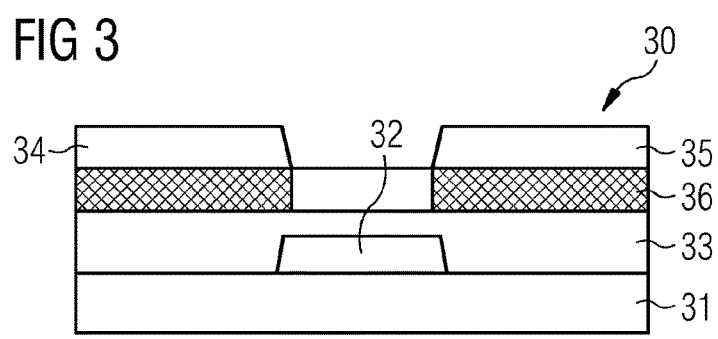

PROAZAPHOSPHATRANES AS N-DOPANTS IN ORGANIC ELECTRONICS

CROSS-REFERENCE TO RELATED APPLICATIONS

This application is a U.S. National Stage Application of International Application No. PCT/EP2015/078921 filed Dec. 8, 2015, which designates the United States of America, and claims priority to DE Application No. 10 2015 200 690.5 filed Jan. 19, 2015, the contents of which are hereby incorporated by reference in their entirety.

FIELD OF THE INVENTION

The present invention relates to an n-dopant for doping organic electron transport materials, wherein the n-dopant comprises at least one proazaphosphatrane compound having a triple N-substituted phosphorus atom of the following Formula 1

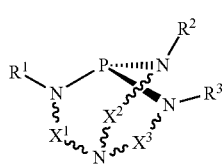

wherein $R^1$-$R^3$ independently of one another are selected from the group R encompassing H, D, C1-C60 saturated or unsaturated alkyl, cycloalkyl, heteroalkyl, heterocycloalkyl, C1-C60 aryl, alkylaryl, heteroaryl, ethers, esters, and $PR'_3$, where the group R' encompasses the substituents of group R without $PR'_3$, where $R^1$-$R^3$ independently of one another may be bridged; $X^1$-$X^3$ independently of one another are selected from the group encompassing a bond and substituted or unsubstituted C1-C10 alkyl, cycloalkyl, aryl, and alkylaryl.

BACKGROUND OF THE INVENTION

For components in organic electronics it is usually the case that the lower the voltage drop over the transport layers with p- (hole) or n- (electron) conductivity that are contained in these components, the greater the efficiency of the components. This functional relationship is valid in particular for organic light-emitting diodes (diagrammatic layer structure shown in FIG. 1) and organic solar cells (FIG. 2). Similar relationships are valid for organic field-effect transistors (FIG. 3), and in these cases in particular the efficiency of the injection of charge carriers is dependent on the level of the contact resistances. If this can be minimized, the effective mobility of the semiconductor is increased. As established in the art, in addition to the use of suitable electrically conducting organic materials, is the introduction into the layers of additional substances whose effect is to increase the intrinsic conductivity of these materials. Depending on the desired aim, a distinction is made between p- and n-dopants, enhancing in each case the p-conductivity and the n-conductivity of transport/contact layers, respectively. The number of n-dopants available for these organic electronic components is very limited, thereby restricting the design possibilities and present technical performance capacity of organic components. As well as the use of suitable dopants in OLEDs, therefore, their utilization in field-effect transistors for contact doping, particularly in the case of complementary circuits and/or bipolar components, is of great importance.

Within the literature there are a number of references which address the synthesis and the properties of phosphazenes in general. One example is the book "Superbases for organic synthesis—guanidines, amidines, phosphazenes and related organocatalysts" by Tsutomo Ishikawa (WILEY, 2009, ISBN: 978-0-470-51800-7). This topical complex is further treated, for example, in Núñez et al., J. Org. Chem. 1996, 61, 8386, which includes a description of the synthesis of hexaimidazolylcyclotriphosphazene. Not cited in these literature references, either for the phosphazenes or, in particular, for the proazaphosphatranes, are fields of use within the sector of organic electronics.

The patent literature recites the use of specifically substituted phosphazenes in organic electronics as electron conductors. Thus, for example, WO 2009/153276 A1 discloses an organic light-emitting diode comprising at least one cyclic phosphazene compound of the following formula

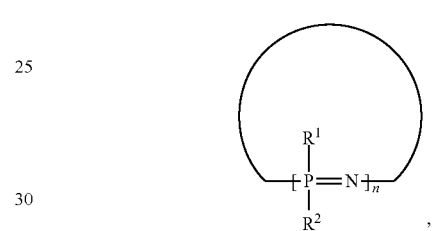

a light-emitting layer composed of at least one matrix material and at least one emitter material, in which the at least one matrix material comprises at least one cyclic phosphazene compound, the use of cyclic phosphazene compounds in organic light-emitting diodes, and a device selected from the group consisting of stationary screens, mobile screens, and lighting units, comprising at least one organic light-emitting diode of the invention and selected cyclic phosphazene compounds, and methods for producing them.

WO 2012 175219 A1 discloses an electronic device which comprises a compound A-B, where

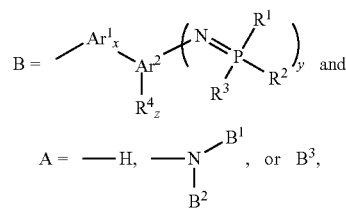

in which —$Ar^1$ is a C6-C18 arylene, which may be mono- or polycyclic and may optionally be substituted by one or more C1-C10 alkyl or C3-C10 cycloalkyl groups, —$Ar^2$ is a C6-C18 arene skeleton, which is optionally substituted by electron-donating groups $R^4$, —$B^1$ and $B^2$ independently are selected from B and $Ar^2$, —$B^3$ independently is selected from the same group as B, —$R^1$, $R^2$, and $R^3$ independently are selected from alkyl, arylalkyl, cycloalkyl, aryl, and dialkylamino, —X is selected from 0, 1, 2, and 3, and for x>1 each $Ar^1$ may be different, —y is a nonzero integer up to the total number of valence sites on the arene skeleton, —z is an integer from zero up to the total number of valence sites on the arene skeleton minus y, and also a corresponding compound of formula AB.

The use of specifically substituted proazaphosphatranes as n-dopants for increasing the conductivity of organic electron conductors, and not as electron conductors themselves, in contrast, is not suggested by the prior art.

SUMMARY OF THE INVENTION

It is therefore an object of the present invention to provide a class of substances which are capable of significantly increasing the conductivity of organic electron conductors by means of doping. A further object of some embodiments of this invention is to provide methods by which n-transport layers having improved conductivity are obtainable, and also the provision of organic-electrical components comprising these transport layers.

According to some embodiments, the invention provides an organic n-dopant for doping organic electron transport materials, the n-dopant comprising at least one proazaphosphatrane compound having a triple N-substituted phosphorus atom of the formula

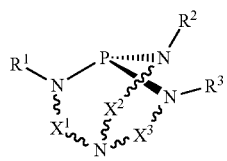

wherein $R^1$-$R^3$ independently of one another are selected from the group R consisting of H, D, C1-C60 saturated or unsaturated alkyl, cycloalkyl, heteroalkyl, heterocycloalkyl, C1-C60 aryl, alkylaryl, heteroaryl, ethers, esters, and $PR'_3$, wherein the group R' encompasses the substituents of group R without $PR'_3$, where $R^1$-$R^3$ independently of one another may be bridged;

$X^1$-$X^3$ independently of one another are selected from the group consisting of a bond and substituted or unsubstituted C1-C10 alkyl, cycloalkyl, aryl, and alkylaryl.

According to some embodiments, the invention provides methods for producing n-conducting organic-electrical layers. The methods may comprise depositing an organic n-dopant together with matrix material within a layer. The n-dopant may comprise at least one proazaphosphatrane compound having a triple N-substituted phosphorus atom of the formula

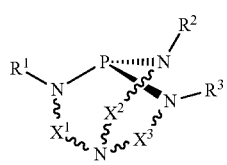

wherein $R^1$-$R^3$ are may independently selected from the group consisting of H, D, C1-C60 saturated or unsaturated alkyl, cycloalkyl, heteroalkyl, heterocycloalkyl, C1-C60 aryl, alkylaryl, heteroaryl, ethers, esters, and $PR'_3$, the group R' may include the substituents of group R without $PR'_3$, $R^1$-$R^3$ independently of one another may be bridged, $X^1$-$X^3$ may be independently selected from the group consisting of a bond and substituted or unsubstituted C1-C10 alkyl, cycloalkyl, aryl, and alkylaryl. Preferably, the n-dopant and the matrix material are reacted.

According to still further embodiments, the invention provides organic-electrical components comprising an organic-electrical layer formed from an n-dopant and an electron-conducting matrix material. Preferably, the n-dopant comprises at least one proazaphosphatrane compound having a triple N-substituted phosphorus atom of the formula

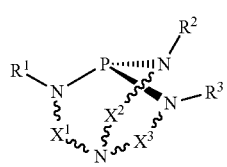

Preferably, the electron-conducting material may be selected from the group consisting of 2,2',2"-(1,3,5-benzinetriyl)tris(1-phenyl-1-H-benzimidazole), 2-(4-biphenylyl)-5-(4-tert-butylphenyl)-1,3,4-oxadiazole, 2,9-dimethyl-4,7-diphenyl-1,10-phenanthroline (BCP), 8-hydroxyquinolinolatolithium, 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7-diphenyl-1,10-phenanthroline (BPhen), 3-(4-biphenylyl)-4-phenyl-5-tert-butylphenyl-1,2,4-triazole,bis(2-methyl-8-quinolinolate)-4-(phenylphenolato)aluminum,6,6'-bis[5-(biphenyl-4-yl)-1,3,4-oxadiazo-2-yl]-2,2'-bipyridyl,2-phenyl-9,10-di(naphthalen-2-yl)anthracene; 2,7-bis[2-(2,2'-bipyridine-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalen-2-yl)-4,7-diphenyl-1,10-phenanthroline,2,9-bis(naphthalen-2-yl)-4,7-diphenyl-1,10-phenanthroline,tris(2,4,6-trimethyl-3-(pyridin-3-yl)phenyl)borane,1-methyl-2-(4-(naphthalen-2-yl)phenyl)-1H-imidazo[4,5-f][1,10]phenanthroline,phenyldipyrenylphosphine oxide,3,3',5,5'-tetra[(m-pyridyl)phen-3-yl]biphenyl,1,3,5-tris[(3-pyridyl)phen-3-yl]benzene,4,4'-bis(4,6-diphenyl-1,3,5-triazin-2-yl)biphenyl,1,3-bis[3,5-di(pyridin-3-yl)phenyl]benzene, diphenylbis(4-(pyridin-3-yl)phenyl)silane, 3,5-di(pyren-1-yl)pyridine,1,3,5-tri(p-pyrid-3-ylphenyl)benzene, 2,4,6-tris(3'-(pyridin-3-yl)biphenyl-3-yl)-1,3,5-triazine, naphthalenetetracarboxylic dianhydride and its imides, perylenetetracarboxylic dianhydride and its imides, and siloles-based materials having a silacyclopentadiene unit. According to some embodiments, the component may be an organic photodiode, a solar cell, a bipolar transistor, a field-effect transistor or an organic light-emitting diode. Preferably, $R^1$-$R^3$ of the proazaphosphatrane compound are independently selected from the group consisting of C1-C60 alkyl, cycloalkyl, heteroalkyl, and heterocycloalkyl groups, C1-C60 aryl, alkylaryl, and heteroaryl groups, ethers, and esters. And $R^1$-$R^3$ may independently of one another be bridged. Further and preferably, $X^1$-$X^3$ of the proazaphosphatrane compound are independently selected from the group consisting of a bond, and C1-C10 alkyl, cycloalkyl, aryl, and alkylaryl groups.

According to some embodiments, the layer is formed by employing least one n-dopant compound of the formulae 2-14:

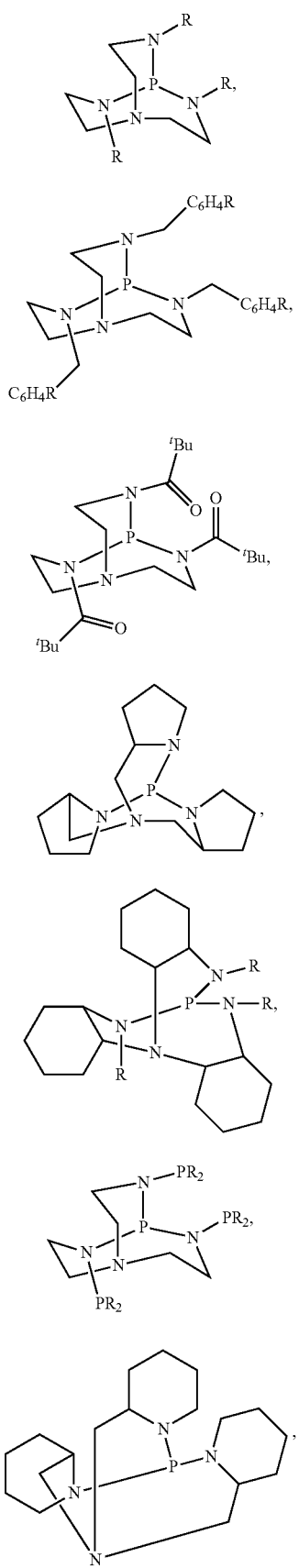

formula 2 formula 3 formula 4 formula 5 formula 6 formula 7 formula 8

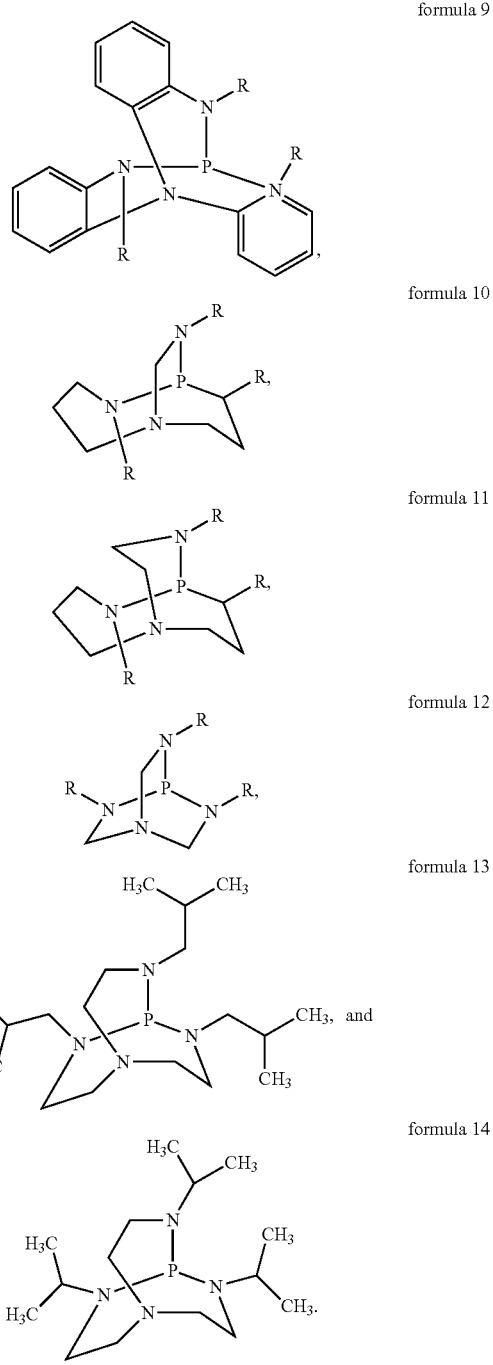

formula 9 formula 10 formula 11 formula 12 formula 13 formula 14

BRIEF DESCRIPTION OF THE FIGURES

The properties of the n-dopants of the invention, and possible embodiments of electrical components in which the dopant may be employed, are elucidated in more detail below using figures as follows:

FIG. 1 shows diagrammatically the structure of an organic light-emitting diode (10). The light-emitting diode is composed of a glass layer (1); silicone or indium-tin oxide (ITO) layer (2); hole injector layer (3); hole transport layer (HTL) (4); emitter layer (EML) (5); hole blocker layer (HBL) (6); electron transport layer (ETL) (7); electron injector layer (8); and a cathode layer (9).

FIG. 2 shows diagrammatically the structure of an organic solar cell with PIN structure (20), which converts light (21) into electrical current. The solar cell consists of a layer of indium-tin oxide (22); a p-doped layer (23); an absorption layer (24); an n-doped layer (25); and a metal layer (26).

FIG. 3 shows diagrammatically a possible cross section of an organic field-effect transistor (30). Applied on substrate (31) is a gate electrode (32), a gate dielectric (33), a source and drain contact (34+35), and an organic semiconductor (36). The shaded areas show the areas at which contact doping is useful.

DETAILED DESCRIPTION OF THE PREFERRED EMBODIMENTS OF THE INVENTION

In accordance with some embodiments of the invention, the n-dopants for doping organic electron transport materials are characterized in that the n-dopants comprise at least one proazaphosphatrane compound having a triple N-substituted phosphorus atom of the following Formula 1:

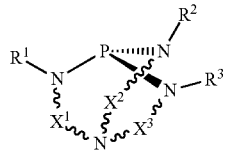

wherein $R^1$-$R^3$ independently of one another are selected from the group R encompassing H, D, C1-C60 saturated or unsaturated alkyl, cycloalkyl, heteroalkyl, heterocycloalkyl, C1-C60 aryl, alkylaryl, heteroaryl, ethers, esters, and $PR'_3$, where the group R' encompasses the substituents of group R without $PR'_3$, where $R^1$-$R^3$ independently of one another may be bridged;

$X^1$-$X^3$ independently of one another are selected from the group encompassing a bond and substituted or unsubstituted C1-C10 alkyl, cycloalkyl, aryl, and alkylaryl.

It has surprisingly been discovered that n-dopants which have a proazaphosphatrane group of Formula 1 are able to produce a significant increase in the electron conductivity of organic electron transport materials. This effect may not be attributable to the intrinsic conductivity of the n-dopants of the invention, but instead may come from the interaction of the n-dopants of the invention with electron transport materials. This significant increase in the conductivity may be obtained not only with substances having only proazaphosphatrane groups as functional units, but also with substances in which the proazaphosphatrane group is only one constituent of the functional groups in the molecule. Without being tied to the theory, it is believed a possible reason for this behavior is that the proazaphosphatranes are very strong bases which in the protonated form, exhibit an extraordinary stability. The proazaphosphatranes may be protonated by acidic hydrogen atoms on the phosphorus atom and not, like the usual phosphazene bases, on a nitrogen atom:

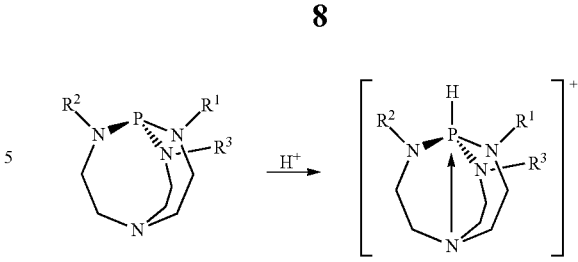

This protonated form (azaphosphatrane) may be stabilized through charge compensation by the nitrogen atom not bonded to the phosphorus atom (transannulation). Transannulation in this case stabilizes the positive charge on the azaphosphatrane by means of the bridgehead nitrogen atom. The N—P spacing in azaphosphatranes is around 2 Å, while in proazaphosphatranes it is around 3 Å. This clearly shows the formation of bonds between the bridgehead N atom and P atoms by protonation (or coordination of a molecule). As illustrated below, a similar mechanism may also take place with other azidic compounds (Z) such as, for example, other matrix materials:

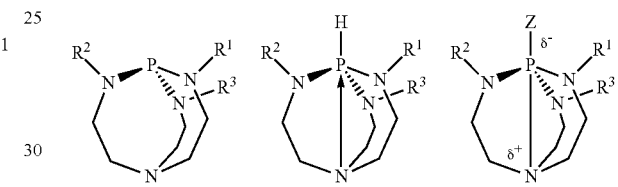

The proazaphosphatrane may therefore be able, for example, to accept an azidic proton from an electron transport material (ETM) and thereby generate the desired negative charge on the ETM. Alternatively, as shown below, the proazaphosphatrane may overall act as an electron pair donor, may coordinate a matrix molecule to the phosphorus, and in so doing may generate a negative (partial) charge on the ETM. Anions and cations may be formed.

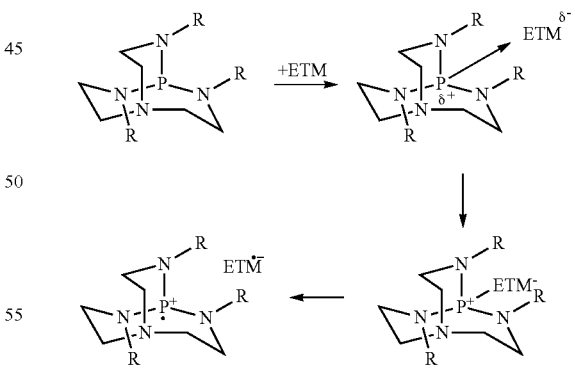

The group-R substituents of some embodiments of the invention appear to be capable of further increasing the basicity of the central phosphorus atom, probably due to their +i effect. Furthermore, these substituents are sufficiently small, thereby enabling unhindered access to the central phosphorus atom. This may lead to particularly rapid kinetics and to effective reaction, for example, with electron transport materials. The selection of the substituents Z in accordance with some embodiments of the invention, as well, appears to result in particularly effective stabilization of the azaphosphatrane. Without being tied to a theory, it is believed that the probable cause of this is that relatively short substituents Z enable effective transannulation. Larger substituents Z, in contrast, may lead to an excessive spacing of the nitrogen atom not bonded to the phosphorus atom, something which may impair charge compensation. As a result of these properties, therefore, the class of substances of the invention may act as an n-dopant. The strong basicity of the compound, accordingly, produces dopants which exhibit an improved doping effect in comparison to the n-dopant of the prior art. The n-dopants of the invention, accordingly, may also be used as a blocking material in p-conductive layers.

A proazaphosphatrane group in the sense of the invention refers to a compound which has at least one proazaphosphatrane group of the Formula 1 in the molecule. This may be a charged molecule or else a salt compound having ions, in which case at least one ion comprises a proazaphosphatrane group. Significant for the proazaphosphatrane group is the attachment of 3 nitrogen atoms to the central phosphorus atom and the attachment of a $4^{th}$ nitrogen atom to the 3 phosphorus-bonded nitrogen atoms. Furthermore, however, it is also possible for the dopant of the invention to have further functional groups as well as the proazaphosphatrane unit.

In accordance with some embodiments of the invention, the substances having at least one proazaphosphatrane group are used as an n-dopant. This means that it is not in accordance with the invention for these substances alone to be used within a layer in an organic electronic component. The reason for this is that the basic conductivity of this class of compounds is insufficient for effective organic-electronic components. This dopant, then, is intended for interaction with an electron transport materials. Here it has been discovered that as well as the strong basicity, the HOMO levels of the n-dopants of the invention appear to be such that they are able to enter effectively into interaction with the LUMO levels of common electron transport materials. A dopant in this context, then, is a substance which is deposited together with the electron transport material by production methods known to the skilled person. It is especially preferred in this context for the molar fraction of the n-dopant in the layer not to be above the molar fraction of the electron transport material. The concentration of the n-dopants of the invention in a layer is usually much lower than that of the electron transport material. Deposited as a single substance in a layer, moreover, the n-dopant of the invention exhibits much lower electrical conductivity than layers comprising electron transport materials. As a result of the joint deposition, the maximum conductivity of the electron transport materials is significantly increased and, furthermore, there is a significantly higher current flow even at lower voltages. Another reason for the n-dopant function is that in p-conducting layers, the n-dopants of the invention act as a blocking material. This is also in contradistinction to electron transport materials.

In one particularly preferred embodiment of the invention, the $X^1$-$X^3$ may independently of one another be selected from the group encompassing a bond and substituted or unsubstituted C1-C6 alkyl, cycloalkyl, aryl, and alkylaryl groups. As already mentioned earlier on above, the short-chain hydrocarbons in particular appear capable of achieving a particularly good n-doping effect. The genesis of this may be that in addition to the aforementioned improved transannulation as a result of the steric properties of small substituents Z, this selection of substituents also exerts a +i effect, which may increase the basicity of the phosphorus atom. Both effects may contribute to a better doping effect of the compound.

In one preferred aspect of some embodiments of the invention, the $X^1$-$X^3$ may independently of one another be selected from the group encompassing a bond and substituted or unsubstituted C1-C5 alkyl groups. The short-chain alkyl substituents for the $X^1$-$X^3$ in particular appear to improve the charge compensation after acceptance of a proton and therefore the stabilization of the base. This may contribute to rapid reaction kinetics and to a shift in equilibrium distinctly to the side of the protonated base.

In one preferred embodiment of the invention, at least one of the $X^1$-$X^3$ may be a substituted or unsubstituted C2 alkyl group. It has emerged that a compound having very short-chain alkyl group may contribute to particularly advantageous positioning of the nitrogen atom not bonded to the phosphorus atom. This may contribute to advantageous transannulation and hence a particularly good doping effect.

In a further refinement according to an embodiment of the invention, each of the $X^1$-$X^3$ may be a substituted or unsubstituted C2 alkyl group. Attachment of the nitrogen atom not bonded to the phosphorus atom to the remaining nitrogen atoms via C2 alkyl groups appears to result in particularly suitable, symmetrical positioning of the non-phosphorus-bonded nitrogen atom, which, after acceptance of a proton, is able to contribute to effective stabilization of the compound. Through this embodiment, therefore, particularly complete reaction with electron transport materials may be achieved, and thus leading to a particularly good doping effect.

In a further aspect of the invention, at least two of the $R^1$-$R^3$ substituents may be joined to one another via a bridge. It may also be advantageous for at least 2 of the nitrogen atoms bonded to the phosphorus atom to be joined to one another via a further bridge. This bridge, probably due to the reduced mobility of the nitrogen atoms bonded to the phosphorus atom, may result in the central phosphorus atom, after acceptance of a proton, being effectively protected from the ingress of further compounds. This may contribute to effective proton transfer and also to a particularly stable base.

In one preferred embodiment of the invention, the n-dopants may have only one proazaphosphatrane group ($PN_4$). In view of the strong basicity of the proazaphosphatrane group, it has proven suitable if the n-dopants of the invention have only one proazaphosphatrane group. With the substitution pattern according to an embodiment of the invention, these compounds produce n-dopants which may be processed effectively with the common production methods for organic layers, both in wet processes and by means of vacuum methods.

In one particular refinement of the invention, the n-dopant may comprise at least one compound of the formulae 2-14 below:

formula 2

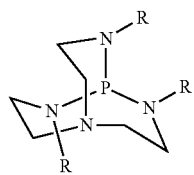

formula 3

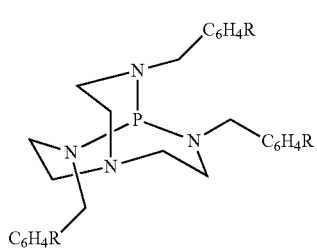

formula 4

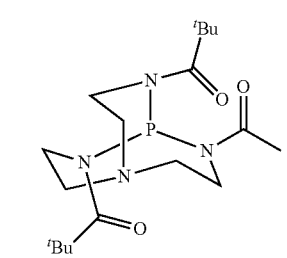

formula 5

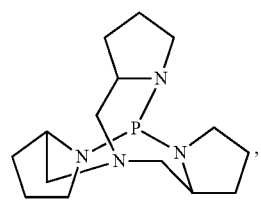

formula 6

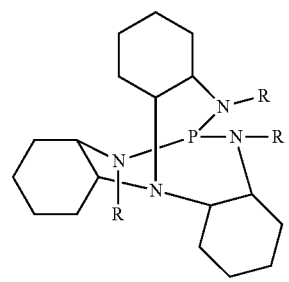

formula 7

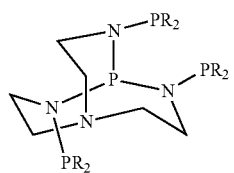

formula 8

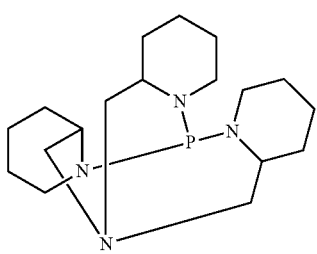

formula 9

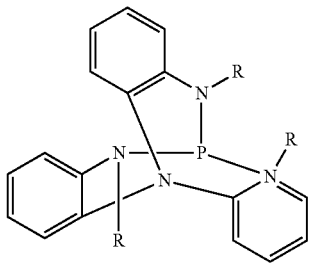

formula 10

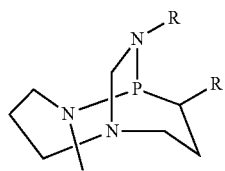

formula 11

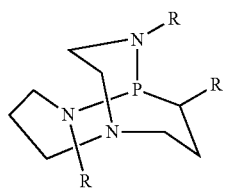

formula 12

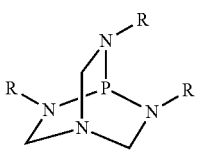

formula 13

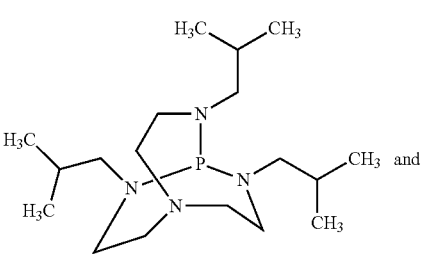 and formula 14

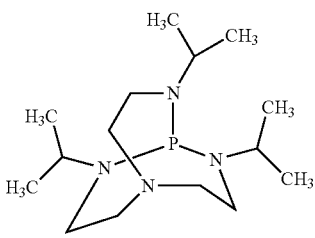

These compounds have proven to be particularly suitable for the doping of electron transport materials, on account of their basicity, their electronic properties, and their molecular weight. A feature of these compounds is a ready solubility, which also enables processing through a wet phase. Accordingly, these compounds may be flexibly employed and used to obtain homogeneous doped layers.

Further in accordance with some embodiments of the invention, methods are provided for producing n-conducting organic-electrical layers, wherein the organic n-dopant of the invention is deposited together with a matrix material within a layer, and the n-dopant and the matrix material are reacted. Without being tied to a theory, it is believed the reaction may take place according to the reaction mechanism indicated earlier above, with the electron transport material giving up a proton to the n-dopant of the invention. At this point, however, a proton need not necessarily be transferred. Alternatively, there may also first be an electrostatic interaction of the n-dopant of the invention with the electron transport material, leading subsequently to a transfer of electrons to the electron transport material. In that case, the reaction may take place automatically, on the basis of suitable reaction kinetics, as a result of the simultaneous deposition in a layer. Depending on the electron transport material selected and the n-dopant employed, the reaction may also be induced by subsequent thermal excitation. For this method, it is possible to use the common electron transport materials which are familiar to the skilled person within organic electronics. Both materials may be deposited from the wet phase and through a vacuum process. The proazaphosphatrane here serves as n-dopant and may develop its doping effect either by co-evaporation with an electron transport material or by mixing of a proazaphosphatrane with an ETM and subsequent liquid processing (e.g., spin coating, inkjet printing, slot coating, etc.). On account of their ready solubility—even in highly apolar solvents—the proazaphosphatrane bases are very suitable for liquid processing. The larger molecules have great thermal stability and can be evaporated in a high vacuum in the particularly preferred temperature range of 150-250° C. without decomposition making them suitable for vacuum processing.

In one particular embodiment of the inventive method, the matrix material may be an electron-conducting matrix material selected from the group encompassing 2,2',2"-(1,3,5-benzinetriyl)tris(1-phenyl-1-H-benzimidazole), 2-(4-biphenylyl)-5-(4-tert-butylphenyl)-1,3,4-oxadiazole; 2,9-dimethyl-4,7-diphenyl-1,10-phenanthroline (BCP), 8-hydroxyquinolinolatolithium; 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7-diphenyl-1,10-phenanthroline (BPhen); 3-(4-biphenylyl)-4-phenyl-5-tert-butylphenyl-1,2,4-triazole; bis(2-methyl-8-quinolinolate)-4-(phenylphenolato)aluminum; 6,6'-bis[5-(biphenyl-4-yl)-1,3,4-oxadiazo-2-yl]-2,2'-bipyridyl; 2-phenyl-9,10-di (naphthalen-2-yl)anthracene; 2,7-bis[2-(2,2'-bipyridine-6-yl)-1,3,4-oxadiazo-5-yl]-9,9-dimethylfluorene; 1,3-bis[2-(4-tert-butylphenyl)-1,3,4-oxadiazo-5-yl]benzene; 2-(naphthalen-2-yl)-4,7-diphenyl-1,10-phenanthroline; 2,9-bis(naphthalen-2-yl)-4,7-diphenyl-1,10-phenanthroline; tris (2,4,6-trimethyl-3-(pyridin-3-yl)phenyl)borane; 1-methyl-2-(4-(naphthalen-2-yl)phenyl)-1H-imidazo[4,5-f][1,10] phenanthroline; phenyldipyrenylphosphine oxide; 3,3',5,5'-tetra[(m-pyridyl)phen-3-yl]biphenyl; 1,3,5-tris[(3-pyridyl)phen-3-yl]benzene; 4,4'-bis(4,6-diphenyl-1,3,5-triazin-2-yl) biphenyl; 1,3-bis[3,5-di(pyridin-3-yl)phenyl]benzene; diphenylbis(4-(pyridin-3-yl)phenyl)silane; 3,5-di(pyren-1-yl)pyridine; 1,3,5-tri(p-pyrid-3-ylphenyl)benzene; 2,4,6-tris (3'-(pyridin-3-yl)biphenyl-3-yl)-1,3,5-triazine; naphthalenetetracarboxylic dianhydride and its imides; perylenetetracarboxylic dianhydride and its imides; materials based on siloles, having a silacyclopentadiene unit. These electron transport materials may be readily reacted with the proazaphosphatrane dopants of the invention, on account of the electronic properties of the materials (HOMO/LUNO level). The additional incorporation of the proazaphosphatranes as dopants can be used to achieve a significant increase in the conductivity of the electron transport materials. Here it may be advantageous for the molar ratio between n-dopant of the invention and the electron transport material to be from ≥0.001 up to ≤1, preferably from ≥0.005 up to ≤0.5, more preferably from ≥0.01 up to ≤0.25. It may therefore be advantageous to use a significant excess of electron transport material and/or a mixture of electron transport materials.

Further in accordance with some embodiments of the invention, an n-conducting organic-electrical layer produced by a method of the invention is provided. The method presented above allows homogeneous layers to be obtained which are suitable for use in components of organic electronics. In this context, as mentioned, the proazaphosphatranes of the invention are especially suitable to be processed by the standard methods of organic electronics. Furthermore, a feature of the layers thus produced is that they have a low crystallization tendency which may contribute to a longer life of organic components containing these layers. Moreover, the increased conductivity of the electron transport layers results in a greater electronic efficiency of the layers.

Also in accordance with the invention is an organic-electrical component, wherein the component comprises an n-conducting organic-electrical layer of the invention. The n-dopants of the invention and the method of the invention for producing doped electron transport layers may be utilized to particularly good effect for the production of organic-electrical components. In this way, long-lived efficient components are obtained.

The layers of the invention may be employed especially in the standard components of organic electronics, namely preferably in the components selected from the group encompassing organic photodiodes, solar cells, bipolar and field-effect transistors, and organic light-emitting diodes. For the components stated above, the n-dopants of the invention may contribute to a significant increase in the electronic efficiency and longevity.

With regard to further advantages and features of the above-described methods, reference is hereby made explicitly to the explanations in connection with the n-dopant of the invention, the layers of the invention, and the components of the invention. Additionally, features of the invention and advantages of the n-dopants of the invention are also intended to be applicable and disclosed for the layers of the invention, the method of the invention, and the organic components of the invention, and vice versa. The invention also embraces all combinations of at least two features disclosed in the description and/or in the claims.

What is claimed is:

1. A method for producing n-conducting organic-electrical layers, the method comprising
    depositing an organic n-dopant together with a matrix material within a layer, wherein the n-dopant comprises at least one proazaphosphatrane compound having a triple N-substituted phosphorus atom of the formula

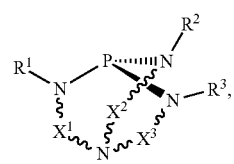

wherein $R^1$-$R^3$ are independently selected from the group consisting of H, D, C1-C60 saturated or unsaturated alkyl, cycloalkyl, heteroalkyl, heterocycloalkyl, C1-C60 aryl, alkylaryl, heteroaryl, ethers, esters, and PR'$_3$, wherein the group R' encompasses the substituents of group R without PR'$_3$, where R$^1$-R$^3$ independently of one another may be bridged; X$^1$-X$^3$ are independently selected from the group consisting of a bond and substituted or unsubstituted C1-C10 alkyl, cycloalkyl, aryl, and alkylaryl, wherein the matrix material is an electron-conducting matrix material selected from the group consisting of 2,2',2"-(1,3,5-benzinetriyl)tris(1-phenyl-1-H-benzimidazole), 2-(4-biphenylyl)-5-(4-tert-butylphenyl)-1,3,4-oxadiazole; 2,9-dimethyl-4,7-diphenyl-1,10-phenanthroline (BCP), 8-hydroxyquinolinolatolithium; 4-(naphthalen-1-yl)-3,5-diphenyl-4H-1,2,4-triazole; 1,3-bis[2-(2,2'-bipyridine-6-yl)-1,3,4-oxadiazo-5-yl] benzene; 4,7-diphenyl-1,10-phenanthroline (BPhen); 3-(4-biphenylyl)-4-phenyl-5-tert-butylphenyl-1,2,4-triazole; bis(2-methyl-8-quinolinolate)-4-(phenylphenolato)aluminum; 6,6'-bis[5-(biphenyl-4-yl)-1,3,4-oxadiazo-2-yl]-2,2'-bipyridyl; 2-phenyl-9,10-di(naphthalen-2-yl)anthracene; 2,7-bis[2-(2,2'-bipyridine-6-yl)-1,3,4-oxadiazo-5-yl]-9,9-dimethylfluorene; 1,3-bis[2-(4-tert-butylphenyl)-1,3,4-oxadiazo-5-yl]benzene; 2-(naphthalen-2-yl)-4,7-diphenyl-1,10-phenanthroline; 2,9-bis(naphthalen-2-yl)-4,7-diphenyl-1,10-phenanthroline; tris(2,4,6-trimethyl-3-(pyridin-3-yl)phenyl) borane; 1-methyl-2-(4-(naphthalen-2-yl)phenyl)-1H-imidazo[4,5-f][1,10]phenanthroline; phenyldipyrenylphosphine oxide; 3,3',5,5'-tetra[(m-pyridyl)phen-3-yl]biphenyl; 1,3,5-tris[(3-pyridyl)phen-3-yl]benzene; 4,4'-bis(4,6-diphenyl-1,3,5-triazin-2-yl)biphenyl; 1,3-bis[3,5-di(pyridin-3-yl)phenyl]benzene; diphenylbis(4-(pyridin-3-yl)phenyl)silane; 3,5-di(pyren-1-yl)pyridine; 1,3,5-tri(p-pyrid-3-ylphenyl)benzene; 2,4,6-tris(3'-(pyridin-3-yl)biphenyl-3-yl)-1,3,5-triazine; naphthalenetetracarboxylic dianhydride and its imides; perylenetetracarboxylic dianhydride and its imides; and materials based on siloles having a silacyclopentadiene unit; and the n-dopant and the matrix material are reacted.

2. An organic-electrical component comprising
an organic-electrical layer formed from the reaction of an n-dopant with an electron-conducting matrix material,
the n-dopant comprising at least one proazaphosphatrane compound having a triple N-substituted phosphorus atom of the formula

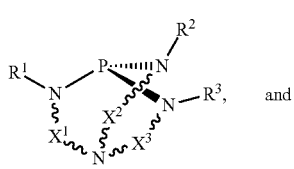

and the electron-conducting matrix material selected from the group consisting of 2,2',2"-(1,3,5-benzinetriyl)tris(1-phenyl-1-H-benzimidazole), 2-(4-biphenylyl)-5-(4-tert-butylphenyl)-1,3,4-oxadiazole, 2,9-dimethyl-4,7-diphenyl-1,10-phenanthroline (BCP), 8-hydroxyquinolinolatolithium, 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7-diphenyl-1,10-phenanthroline (BPhen), 3-(4-biphenylyl)-4-phenyl-5-tert-butylphenyl-1,2,4-triazole,bis(2-methyl-8-quinolinolate)-4-(phenylphenolato)aluminum,6,6'-bis[5-(biphenyl-4-yl)-1,3,4-oxadiazo-2-yl]-2,2'-bipyridyl,2-phenyl-9,10-di(naphthalen-2-yl)anthracene; 2,7-bis[2-(2,2'-bipyridine-6-yl)-1,3,4-oxadiazo-5-yl]-9,9-dimethylfluorene, 1,3-bis[2-(4-tert-butylphenyl)-1,3,4-oxadiazo-5-yl]benzene,2-(naphthalen-2-yl)-4,7-diphenyl-1,10-phenanthroline,2,9-bis(naphthalen-2-yl)-4,7-diphenyl-1,10-phenanthroline,tris(2,4,6-trimethyl-3-(pyridin-3-yl)phenyl)borane, 1-methyl-2-(4-(naphthalen-2-yl)phenyl)-1H-imidazo[4,5-f][1,10]phenanthroline, phenyldipyrenylphosphine oxide,3,3',5,5'-tetra[(m-pyridyl)phen-3-yl]biphenyl,1,3,5-tris[(3-pyridyl)phen-3-yl]benzene,4,4'-bis(4,6-diphenyl-1,3,5-triazin-2-yl) biphenyl, 1,3-bis[3,5-di(pyridin-3-yl)phenyl]benzene, diphenylbis(4-(pyridin-3-yl)phenyl)silane, 3,5-di(pyren-1-yl)pyridine, 1,3,5-tri(p-pyrid-3-ylphenyl)benzene, 2,4,6-tris(3'-(pyridin-3-yl)biphenyl-3-yl)-1,3,5-triazine, naphthalenetetracarboxylic dianhydride and its imides, perylenetetracarboxylic dianhydride and its imides, and siloles-based materials having a silacyclopentadiene unit, wherein the component is selected from the group of components consisting of organic photodiodes, solar cells, bipolar transistors, field-effect transistors, and organic light-emitting diodes.

3. An organic-electrical component according to claim 2, wherein R$^1$-R$^3$ are independently selected from the group consisting of C1-C60 alkyl, cycloalkyl, heteroalkyl, and heterocycloalkyl groups, C1-C60 aryl, alkylaryl, and heteroaryl groups, ethers, and esters.

4. An organic-electrical component according to claim 3, wherein R$^1$-R$^3$ independently of one another may be bridged.

5. An organic-electrical component according to claim 3, wherein X$^1$-X$^3$ are independently selected from the group consisting of a bond, and C1-C10 alkyl, cycloalkyl, aryl, and alkylaryl groups.

6. An organic-electrical component according to claim 3, wherein the layer was formed by a reaction including at least one n-dopant compound of the formulae 2-14:

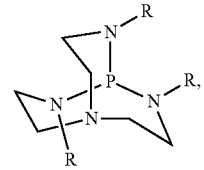

formula 2

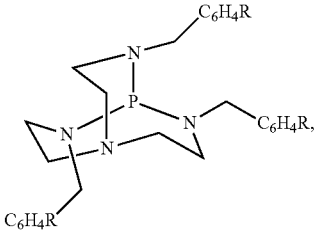

formula 3

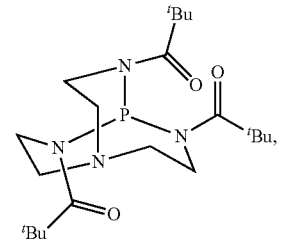

formula 4

-continued
formula 5
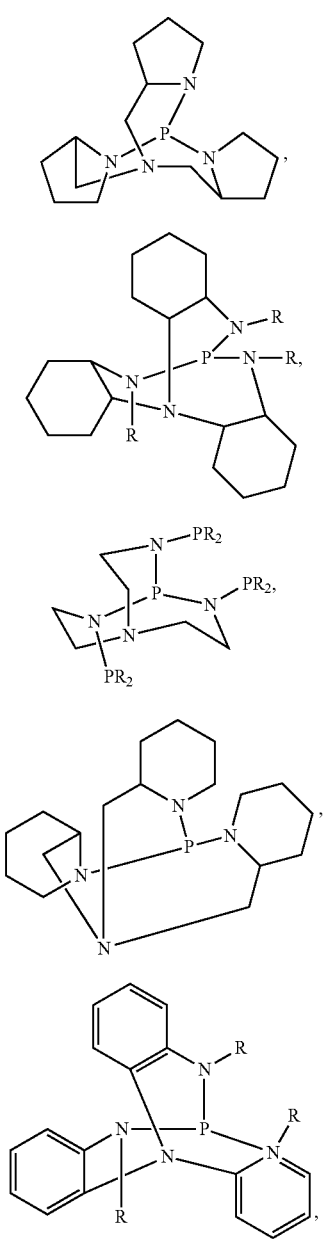
formula 6
formula 7
formula 8
formula 9
formula 10
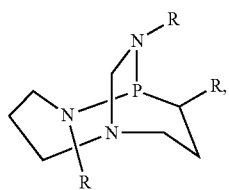
formula 11
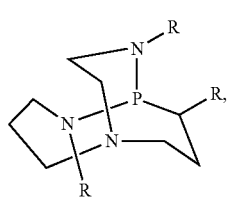
formula 12
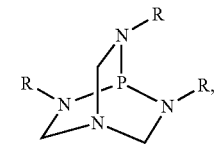
formula 13
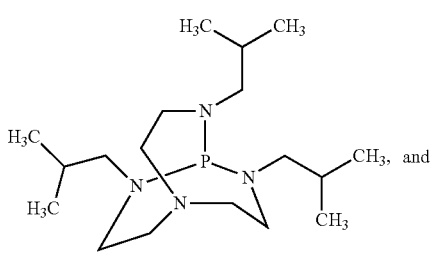
formula 14
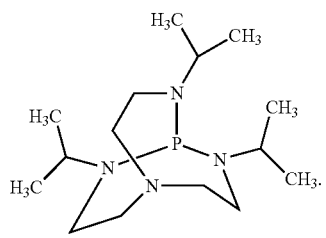
* * * * *